United States Patent [19]

Asakura et al.

[11] Patent Number: 4,706,637
[45] Date of Patent: Nov. 17, 1987

[54] OXYGEN CONCENTRATION SENSING DEVICE FOR AN AIR-FUEL RATIO CONTROL SYSTEM OF AN AUTOMOTIVE INTERNAL COMBUSTION ENGINE

[75] Inventors: Masahiko Asakura, Tokorozawa; Tomohiko Kawanabe, Utsunomiya; Noritaka Kushida, Tokyo; Hiroshi Hasebe, Hatogaya, all of Japan

[73] Assignee: Honda Giken Kogyo Kabushiki Kaisha, Tokyo, Japan

[21] Appl. No.: 843,951

[22] Filed: Mar. 25, 1986

[30] Foreign Application Priority Data

Apr. 25, 1985 [JP] Japan ................................. 60-89647

[51] Int. Cl.$^4$ ...................... F02M 23/06; F02M 23/08
[52] U.S. Cl. .................................. 123/589; 204/406; 204/426
[58] Field of Search ....................... 123/440, 489, 589; 204/406, 424, 425, 426; 60/276

[56] References Cited

U.S. PATENT DOCUMENTS

| | | | |
|---|---|---|---|
| 4,306,957 | 12/1981 | Ishitani et al. | 204/426 X |
| 4,578,172 | 3/1986 | Yamada et al. | 123/489 X |
| 4,586,476 | 5/1986 | Asayama et al. | 204/426 X |
| 4,615,787 | 10/1986 | Yamada et al. | 123/440 X |

*Primary Examiner*—Willis R. Wolfe, Jr.
*Attorney, Agent, or Firm*—Pollock, Vande Sande and Priddy

[57] ABSTRACT

An oxygen concentration sensing device for use in an air-fuel ratio control system of an internal combustion engine includes a pair of solid electrolyte members having oxygen ion permeability which are disposed in the exhaust gas of the engine and arranged to face each other forming a predetermined gap portion between them. Each of the solid electrolyte members is provided with a pair of electrodes. One of the solid electrolyte members is operative as an oxygen pump element when a predetermined constant electric current is supplied across the electrodes thereof. An electric potential developed across the electrodes of the other one of the solid electrolyte members operative as a cell element is supplied to a comparing means in which the input signal from the solid electrolyte member is compared with a predetermined reference potential and a result of comparison is provided as an oxygen concentration detection signal. In an application of the oxygen concentration sensing device according to the invention in an air-fuel ratio control system, the magnitude of the constant current supplied to the oxygen pump element is varied with the value of a target air-fuel ratio which is controlled in response to various operational parameters of the engine.

2 Claims, 10 Drawing Figures

OXYGEN CONCENTRATION SENSING DEVICE FOR AN AIR-FUEL RATIO CONTROL SYSTEM OF AN AUTOMOTIVE INTERNAL COMBUSTION ENGINE

BACKGROUND OF THE INVENTION

1. Field of the Invention

The present invention relates to a system for detecting an oxygen concentration in exhaust gas of an automotive engine, and more particularly to an oxygen concentration sensing device for use in an air fuel-ratio feedback control system for an automotive internal combustion engine.

2. Description of Background Information

Air-fuel ratio feedback control systems for an internal combustion engine are generally constructed such that the oxygen concentration in the exhaust gas of the engine is detected by an oxygen concentration sensor and the air-fuel ratio of the mixture to be supplied to the engine is feedback controlled in response to a result of the detection of the oxygen concentration so as to purify the exhaust gas and improve the fuel economy.

As an example of an oxygen concentration sensing device for use in an air-fuel ratio control system of this type, an oxygen concentration sensing device having an output signal whose level is proportional to the oxygen concentration in test gas (whose oxygen concentration is to be measured) is described in Japanese patent application laid open No. 58-153155. This oxygen concentration sensing device has a sensor element whose general construction includes a pair of flat solid electrolyte members having oxygen ion permeability. These solid electrolyte members are placed in the atmosphere of the test gas. Further, two electrodes are provided on the front and back surfaces of both of the solid electrolyte members. These two solid electrolyte members each having a pair of electrodes are arranged in face to face relation with each other to form a gap portion between them.

With this arrangement, one of the solid electrolyte members serves as an oxygen pump element and the other one of the solid electrolyte members serves as a cell element for sensing an oxygen concentration ratio. A drive current is supplied accross the electrodes of the oxygen pump element in such a way that the electrode facing the gap portion is supplied with the negative current in the atmosphere of the test gas. By the supply of this current, the oxygen gas component of the gas within the gap portion is ionized on the surface of the negative electrode of the solid electrolyte member serving as the oxygen pump element. The oxygen ions migrate through the inside of the oxygen pump element to the positive electrode, where they are released from the surface of the positive electrode in the form of the oxygen gas.

While this movement of oxygen ions occurs, an electric potential is generated across the electrodes of the solid electrolyte member operating as the cell element because the oxygen concentration is different for the gas in the gap portion and the gas outside the electrodes of the cell element. This difference of the oxygen concentration is caused by a reduction of the oxygen gas component within the gap portion. Then, if the magnitude of the electric current supplied to the cell element is varied so as to maintain the potential across the cell element, the magnitude of the electric current varies substantially linearly in proportion to the oxygen concentration of the test gas at room temperature.

FIG. 1 shows an example of a conventional oxygen concentration sensing device of the oxygen concentration proportional type. In this system, an oxygen concentration sensor which is generally designated at $1'$ includes a cell element $2'$ which is provided with a pair of planar electrodes $2a'$ and $2b'$. An electric potential developed across the electrodes $2a'$ and $2b'$ is supplied to a differential amplifier 4 to which a predetermined reference potential $V_r$ (40 mV, for example) is also supplied. The differential amplifer 4 produces an output signal whose level varies with a difference between the electric potential of the cell element $2'$ and the reference potential. The output signal of the difference amplifier 4 is in turn supplied to a V/I converter 5 whose input terminal is connected to an output terminal of the differential amplifier 4. The V/I converter 5 supplies an electric current whose magnitude varies with the output signal level of the differential amplifier 4, across the electrodes $3a'$ and $3b'$ of the oxygen pump element $3'$. The magnitude of the current supplied to the oxygen pump element $3'$ is detected by a current detection circuit 6, and the detected magnitude of current is then utilized as an oxygen concentration detection output signal.

The operation of this conventional device is such that an electric current $I_P$ is supplied from the V/I converter 5 to the oxygen pump element $3'$ so that the electric potential developed at the cell element $2'$ becomes equal to the reference potential. Therefore, an output signal whose level is proportional to the oxygen concentration of the test gas which is typically shown in FIG. 2 of the accompanying drawings can be obtained by detecting the magnitude of the current from the V/I converter 5.

However, in this type of conventional oxygen concentration detection device, a problem was that the structure of the system tends to be complicated, because in addition to the oxygen concentration sensor, various components such as the differential amplifier, the V/I converter, and the current detection circuit are required in order to produce an output signal whose level is substantially proportional to the oxygen concentration. Further, for use in an air/fuel ratio control system, the device requires comparing means for comparing an output signal level of the current detection circuit with a level corresponding to a target air/fuel ratio.

OBJECTS AND SUMMARY OF THE INVENTION

An object of the present invention is therefore to provide an oxygen concentration detection device of the oxygen concentration proportional type having a relatively simple construction and capable of producing a comparison signal between the air/fuel ratio of the supplied mixture and a target air/fuel ratio.

According to the present invention, the oxygen concentration detection device comprises current supply means for supplying a current across the electrodes of the oxygen pump element, and comparing means for comparing an electric potential developing across the terminals of the cell element with a reference potential, to produce a signal indicative of a result of the comparison.

BRIEF DESCRIPTION OF THE DRAWINGS

FIGS. 6 through 8 are flowcharts showing the manner of operation of a CPU 37 in the control circuit 21 in a first embodiment of the air-fuel rato control system according to the present invention, in which FIG. 6 shows a main routine, FIG. 7 shows an A/F routine, and FIG. 8 shows a target air-fuel ratio setting subroutine respectively;

DETAILED DESCRIPTION OF THE PREFERRED EMBODIMENTS

Referring to FIGS. 3 through 10 of the accompanying drawings, the embodiment of the oxygen concentrtion sensing device and its use in the air-fuel ratio control system will be explained hereinafter.

Figure 1:
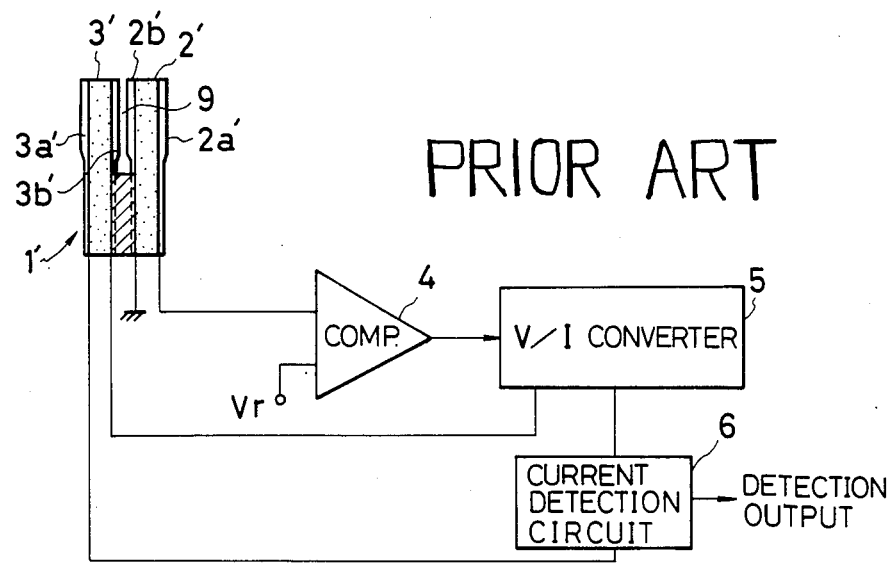
FIG. 1 is a block diagram showing an example of a conventional oxygen concentration sensing device.
Figure 2:
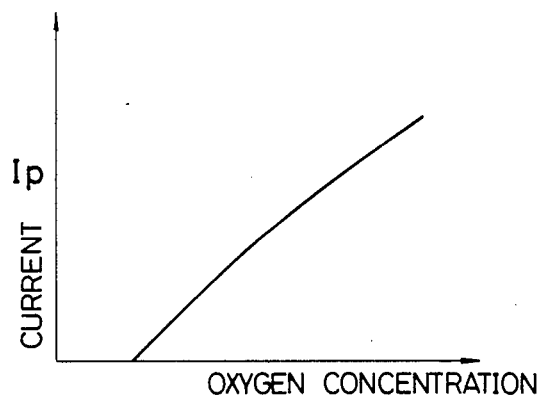
FIG. 2 is a diagram showing an output characteristic of the conventional oxygen concentration sensing device shown in FIG. 1.
Figure 3:
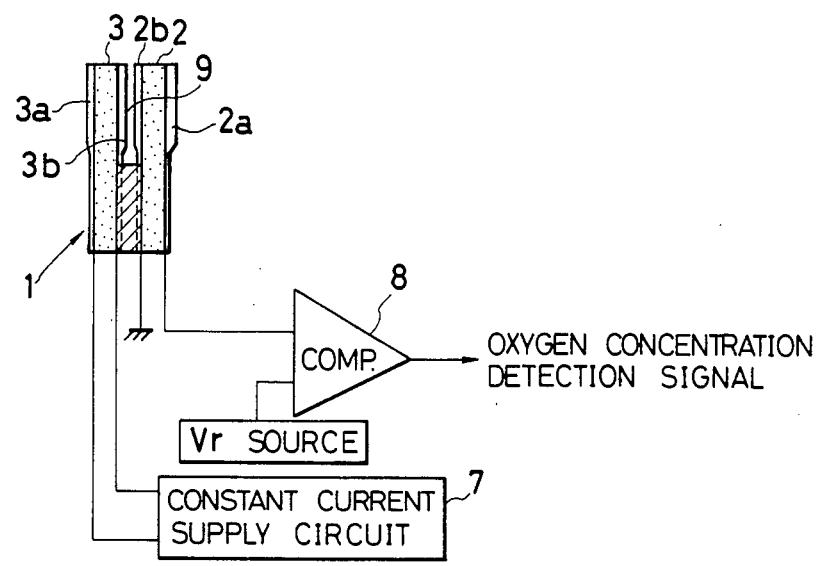
FIG. 3 is a block diagram showing an embodiment of the oxygen concentration sensing device according to the present invention.

Referring first to FIG. 3, the embodiment of the oxygen concentration detection device according to the present invention will be explained in detail.

This oxygen concentration sensing device has a sensor element whose has general construction uses a pair of flat conductive solid electrolyte members. These solid electrolyte members are placed in the atmosphere of the test gas. Further, each solid electrolyte member is provided with a pair of electrodes on its front and back surfaces. These two solid electrolyte members are arranged in face to face relation with each other to form a gap portion between them.

As in the case of the conventional device, one of the solid electrolyte members serves as an oxygen pump element and the other one of the solid electrolyte members serves as a cell element for sensing an oxygen concentration ratio.

More specifically, as shown in FIG. 3, the oxygen concentration sensor is generally designated at 1. The oxygen concentration sensor 1 includes a pair of solid electrolyte members 2 and 3, operating as a cell element and an oxygen pump element respectively. Therefore, the solid electrolyte members 2 and 3 will be referred to as the cell element 2 and the oxygen pump element 3 hereinafter. The cell element 2 has a pair of planar electrodes 2a and 2b and the oxygen pump element 3 has a pair of planar electrodes 3a and 3b.

A constant current source 7 is provided and a constant current from the constant current source 7 is supplied across the electrodes 3a and 3b of the oxygen pump element 3. The magnitude of this constant current is determined in response to a target air/fuel ratio. On the other hand, an electric potential developed across the electrodes 2a and 2b of the cell element 2 is supplied to one of input terminals of a comparator 8. The other one of the input terminals of the comparator 8 is supplied with a reference voltage Vr. An output signal of the comparator 8 is utilized as an output signal of the subject device.

In the thus constructed oxygen concentration detection device according to the present invention, the electric potential $VO_2$ developing across the electrodes 2a and 2b of the cell element 2 represents the difference of the oxygen concentration between the gas in the gap portion 9 and the gas outside of the cell element 2 because the constant electric current is supplied to the electrodes 3a and 3b of the oxygen pump element 3 from the constant current source 7. In other words, the electric potential $VO_2$ whose level is proportional to the oxygen concentration in the exhaust gas of the engine is obtained by the above arrangement when the device is fitted in the exhaust system of an automotive engine. The level of this electric potential increases as the air/fuel ratio of the mixture supplied to the engine becomes richer. When the electric potential $VO_2$ is greater than the reference potential corresponding to the target air-fuel ratio, the comparator 8 produces a high level output signal to indicate that the air-fuel ratio of the mixture supplied to the engine is richer than the target air-fuel ratio. Conversely, when the electric potential $VO_2$ is lower than the reference potential Vr, the comparator 8 produces a low level output signal to indicate that the air-fuel ratio of the mixture is leaner than the target air-fuel ratio. The magnitude of the current from the constant current source 7 to the oxygen pump element 3 is set in response to the target air-fuel ratio, while the reference potential Vr is maintained constant although the target air-fuel ratio is changed depending on the operating condition. With this arrangement, the output signal of the comparator 8 represents the deviation of the air-fuel ratio of the mixture from the target air-fuel ratio.

Figure 4:
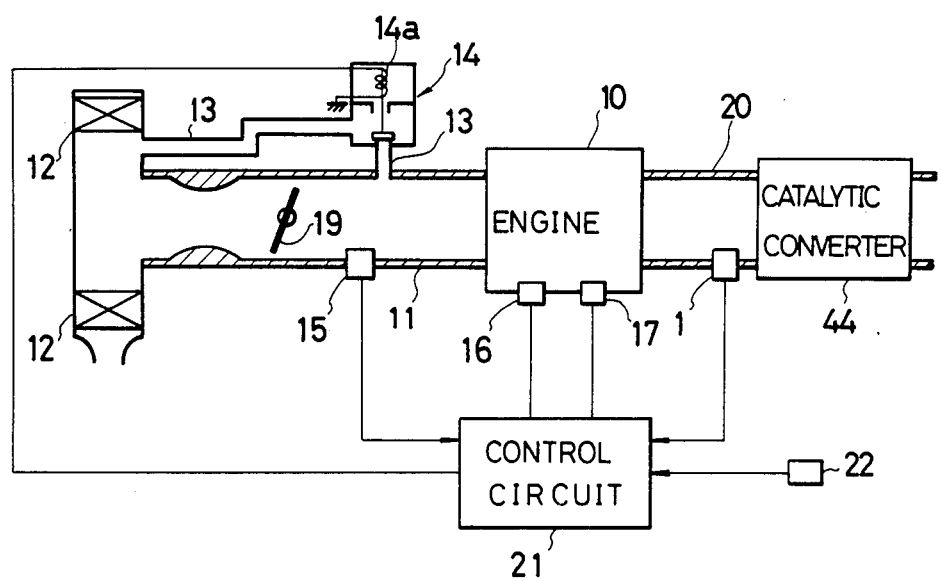
FIG. 4 is a schematic diagram showing the general construction of an example of an air-fuel ratio control system which is provided with the oxygen concentration sensing device according to the invention.

FIG. 4 illustrates a general construction of the air intake side secondary air supply system for an internal combustion engine in which the oxygen concentration sensing device according to the present invention is utilized. The internal combustion engine is generally denoted at 10. An intake air is supplied to the internal combustion engine 10 through an air cleaner 12 and an intake manifold 11. An inside of the air cleaner 12, near an air outlet port, communicates with a part of the intake manifold 11 downstream from a throttle valve 19 of a carburetor via an air intake side secondary air supply passage 13. The air intake side secondary air supply passage 13 is provided with an open/close solenoid valve 14. The open/close solenoid valve 14 is designed to open when a drive current is supplied to a solenoid 14a thereof.

The system also includes an absolute pressure sensor 15 which is provided in the intake manifold 11 for producing an output signal whose level corresponds to an absolute pressure within the intake manifold 11, a crank angle sensor 16 which produces pulse signals in response to the revolution of an engine crankshaft (not shown), and an engine cooling water temperature sensor 17 which produces an output signal whose level corresponds to the temperature of engine cooling water. An oxygen concentration sensor ($O_2$ sensor) 1 which is identical with the oxygen concentration sensor 1 illustrated in FIG. 3 is provided in an exhaust manifold 20 of the engine for generating an output signal whose level varies in proportion to an oxygen concentration in the exhaust gas.

Further, a catalytic converter 44 for accelerating the reduction of the noxious components in the exhaust gas is provided in the exhaust manifold 20 at a location on the downstream side of the position of the O$_2$ sensor 1. The open/close solenoid valve 14, the absolute pressure sensor 15, the crank angle sensor 16, the engine cooling water temperature sensor 17, and the O$_2$ sensor 1 are electrically connected to a control circuit 21. Further, a vehicle speed sensor 22 which produces an output signal whose level is proportional to the speed of the vehicle is electrically connected to the control circuit 21.

Figure 5:
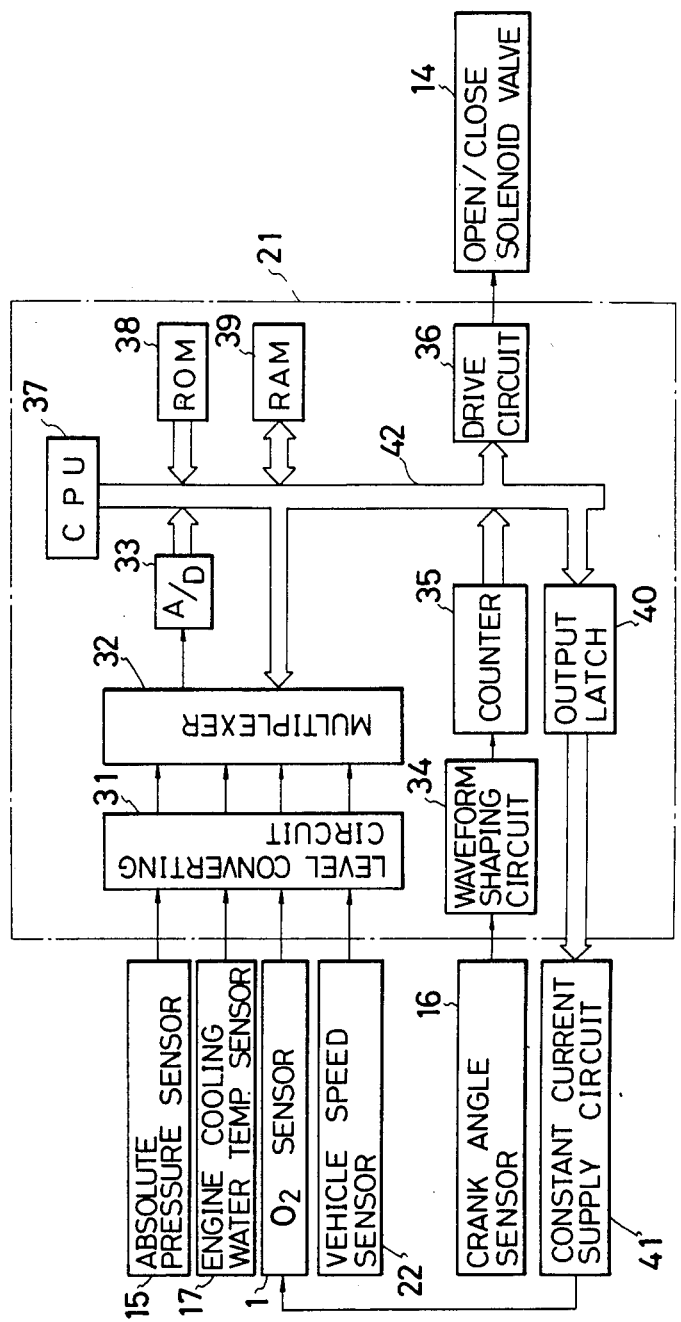
FIG. 5 is a block diagram showing a detail of the construction of the control circuit 21 of the system of FIG. 4.

FIG. 5 shows the construction of the control circuit 21. As shown, the control circuit 21 includes a level converting circuit 31 which effects a level conversion of the output signals of the absolute pressure sensor 15, the engine cooling water temperature sensor 17, the O$_2$ sensor 1, and the vehicle speed sensor 22. Output signals provided from the level converting circuit 31 are in turn supplied to a multiplexer 32 which selectively outputs one of the output signals from each sensor passed through the level converting circuit 31. The output signal provided by the multiplexer 32 is then supplied to an A/D converter 33 in which the input signal is converted into a digital signal. The control circuit 21 further includes a waveform shaping circuit 34 which effects a waveform shaping of the output signal of the crank angle sensor 11, to provide TDC signals in the form of pulse signals. The TDC signals from the waveform shaping circuit 34 are in turn supplied to a counter 35 which counts intervals of the TDC signals. The control circuit 21 includes a drive circuit 36 for driving the open/close solenoid valve 14 in an opening direction, a CPU (central processing unit) 37 which performs digital operations according to various programs, a ROM 38 in which various operating programs and data are previously stored, and a RAM 39. The multiplexer 32, the A/D converter 33, the counter 35, the drive circuit 36, the CPU 37, the ROM 38, the RAM 39, and an output latch 40 are mutually connected via an input-/output bus 42.

The ouput latch 40 is connected to a constant current supply circuit 41 which provides a constant current, corresponding to the digital signal held by the output latch 40, to the oxygen pump element of the O$_2$ sensor 1. In addition, the comparator 8 shown in FIG. 3 is not shown in FIG. 5 since the block diagram representation of the O$_2$ sensor 1 in FIG. 5 represents a combination of an oxygen concentration sensor and a comparator typically illustrated in FIG. 3.

In the thus constructed control circuit 21, information regarding the absolute pressure in the intake manifold 11, the engine cooling water temperature, the oxygen concentration in the exhaust gas, and the vehicle speed, is selectively supplied from the A/D converter 33 to the CPU 37 via the input/output bus 42. Also information indicative of the engine speed from the counter 35 is supplied to the CPU 37 via the input/output bus 42. The CPU 37 is constructed to generate an internal interruption signal every one duty period T$_{SOL}$ (100 m sec, for instance). In response to this internal interruption signal, the CPU 37 performs an operation for the duty ratio control of the air intake side secondary air supply, explained hereinafter.

Figure 6:
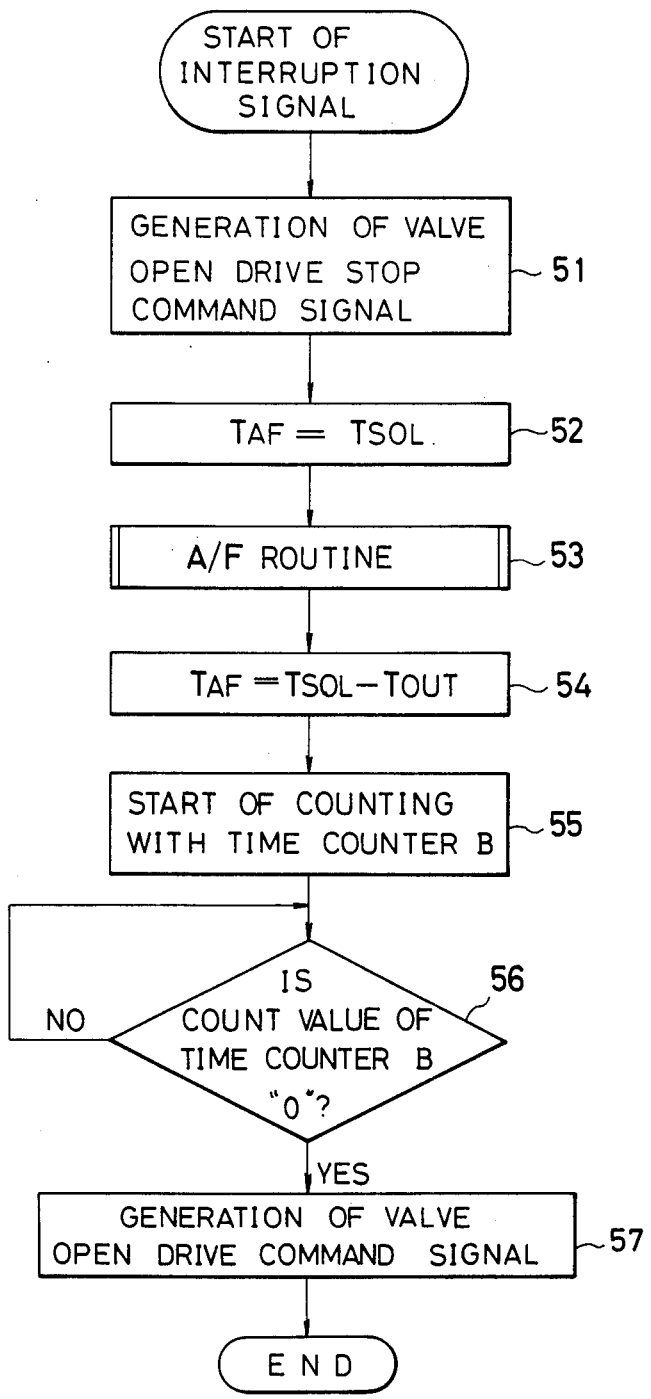
Figure 7:
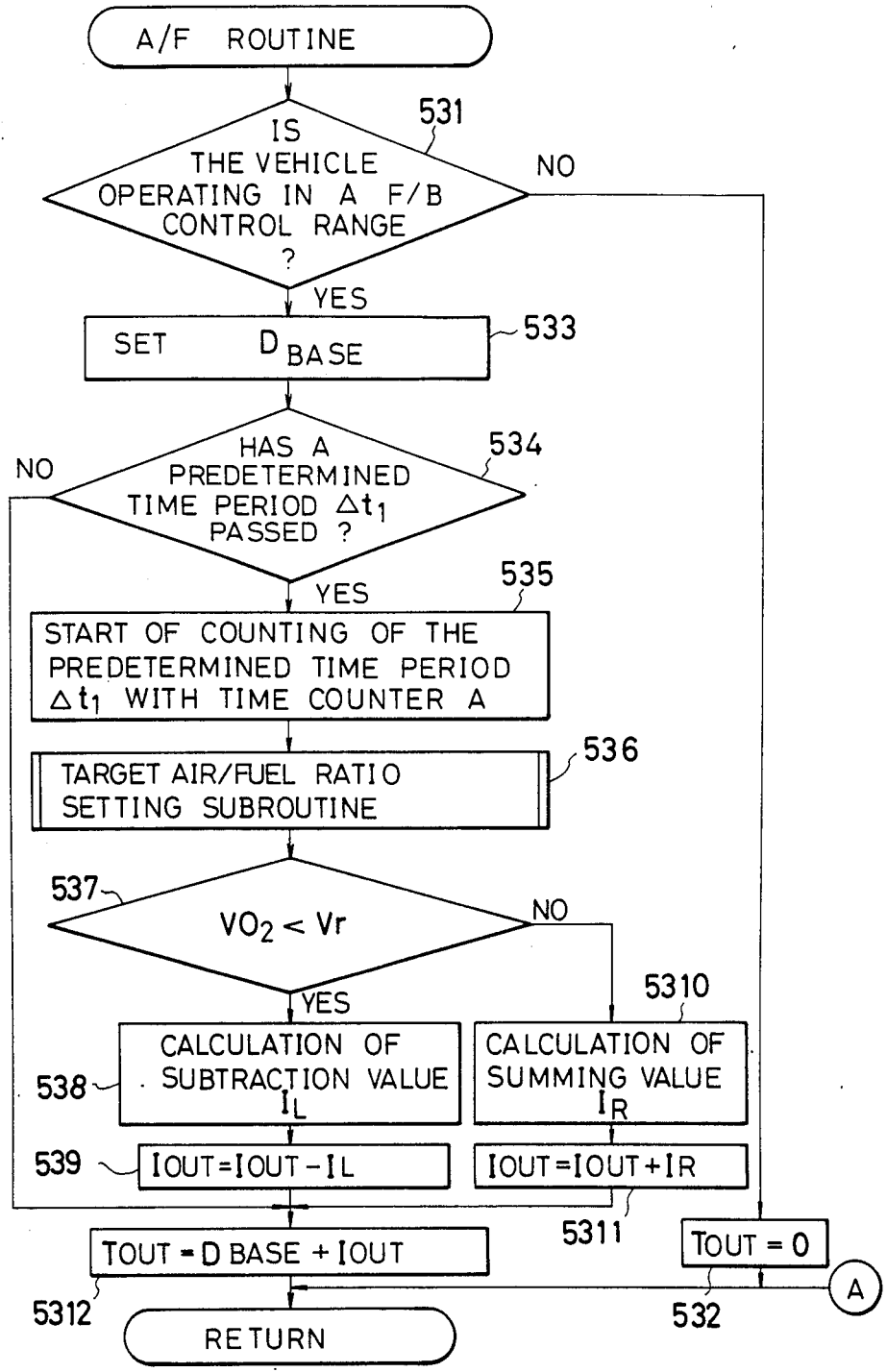
Figure 8:
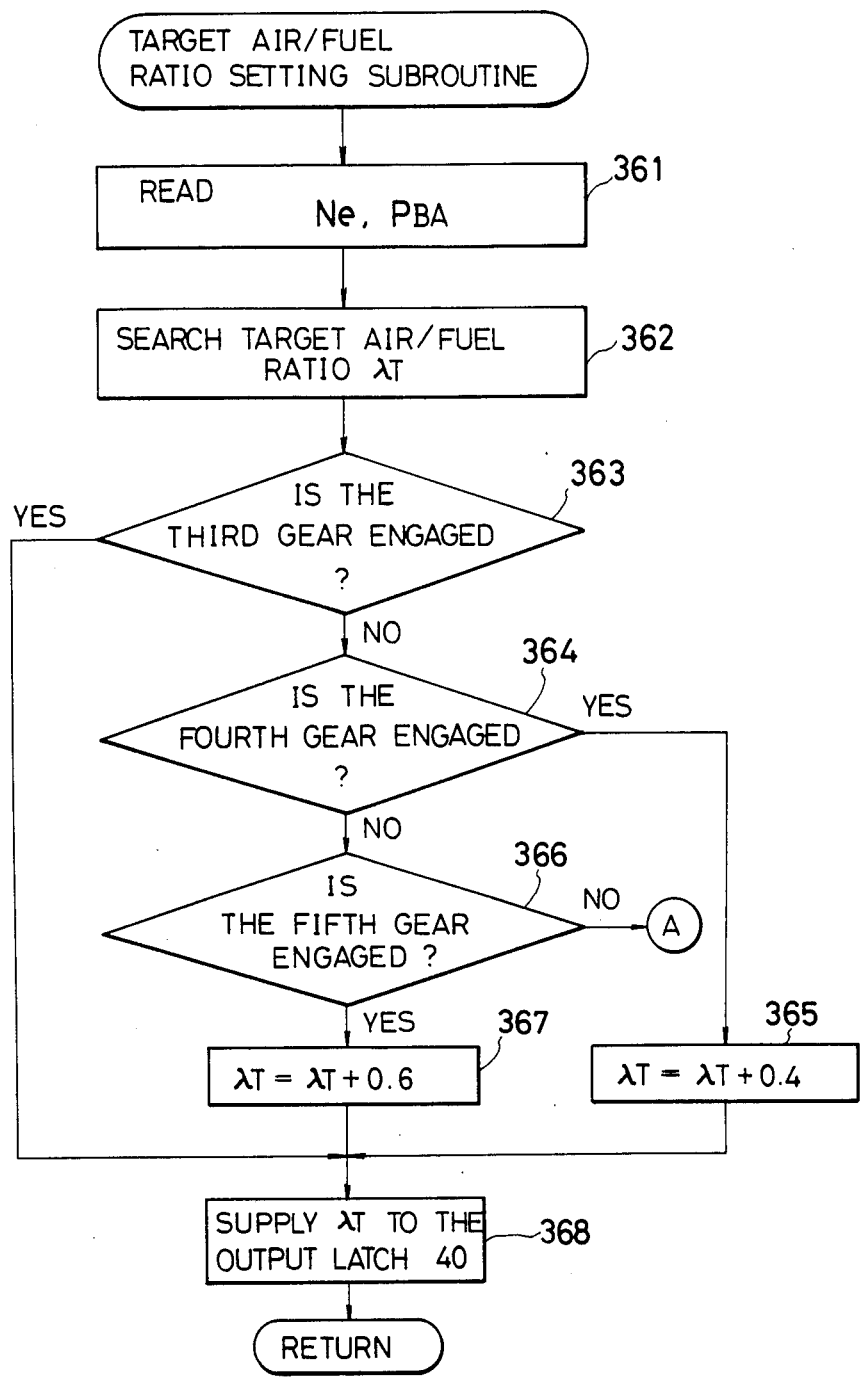

Referring to the flowcharts of FIG. 6 through FIG. 8, the operation of the air-fuel ratio control system according to the present invention will be explained hereinafter.

At a step 51, a valve open drive stop command signal is generated in the CPU 37 and supplied to the drive circuit 36 every time the internal interruption signal in generated in the CPU 37. With this command signal, the drive circuit 36 is controlled to close the open/close solenoid valve 14. This operation is provided so as to prevent malfunctions of the open/close solenoid valve 14 during the calculating operation of the CPU 37. Next, a valve close period T$_{AF}$ of the open/close solenoid valve 14 is made equal to a period of one duty cycle T$_{SOL}$ at a step 52, and an A/F routine for calculating a valve open period T$_{OUT}$ of the open/close solenoid valve 14 which is shown in FIG. 7 is carried out through steps generally indicated at 53.

Figure 9:
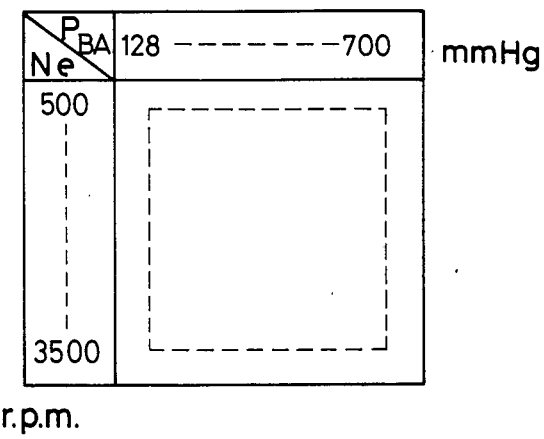
FIG. 9 is a diagram showing a data map which is stored in a ROM 38 of the control circuit 21.

In the A/F routine, whether or not the operating state of the vehicle (including operating states of the engine) satisfies a condition for the feedback (F/B) control is detected at a step 531. This detection is performed according to various parameters, i.e., absolute pressure within the intake manifold, engine cooling water temperature, vehicle speed, and engine rotational speed. For instance, when the vehicle speed is low, or when the engine cooling water temperature is low, it is determined that the condition for the feedback control is not satisfied. If it is determined that the condition for the feedback control is not satisfied, the valve open period T$_{OUT}$ is made equal to "0" at a step 532 to stop the air-fuel ratio feedback control. On the other hand, if it is determined that the condition for the feedback control is satisfied, the supply of the secondary air within the period of one duty cycle T$_{SOL}$, i.e., a period of base duty ratio D$_{BASE}$ for the opening of the open/close solenoid valve 14 is set at a step 533. Various values of the period of base duty ratio D$_{BASE}$ which are determined according to the absolute pressure within the intake manifold P$_{BA}$ and the engine speed N$_e$ are previously stored in the ROM 38 in the form of a D$_{BASE}$ data map as shown in FIG. 9, and the CPU 37 firstly reads current values of the absolute pressure P$_{BA}$ and the engine speed N$_e$ and in turn searches a value of the period of base duty ratio D$_{BASE}$ corresponding to the read values from the D$_{BASE}$ date map in the ROM 38. Then, whether or not a count period of a time counter A incorporated in the CPU 37 (not shown) has reached a predetermined time period $\Delta$ t$_1$ is detected at a step 534. This predetermined time period $\Delta$t$_1$ corresponds to a delay time from a time of the supply of the air intake side secondary air to a time in which a result of the supply of the air intake side secondary air is detected by the O$_2$ sensor 1 as a change in the oxygen concentration of the exhaust gas. When the predetermined time period $\Delta$t$_1$ has passed after the time counter A is reset to start the counting of time, the counter is reset again, at a step 535, to start the counting of time from a predetermined initial value. In other words, a detection as to whether or not the predetermined time period $\Delta$t$_1$ has passed after the start of the counting of time from the initial value by the time counter A, i.e. the execution of the step 535, is performed at the step 534. After the start of the counting of the predetermined time period $\Delta$t$_1$ by the time counter A in this way, a target air-fuel ratio setting subroutine shown in FIG. 8 for setting a target air-fuel ratio is executed through steps generally indicated at 536.

In the target air-fuel ratio setting subroutine in this embodiment, current values of the engine speed N$_e$ and the absolute pressure P$_{BA}$ are read at a step 361. Then a value of the target air-fuel ratio $\lambda_T$ is searched from the A/F data map prepared in the ROM 38 at a step 362. In the ROM 38, various values for the target air-fuel ratio $\lambda_T$ which is determined according to the values of the absolute pressure within the intake manifold $P_{BA}$ and the engine speed $N_e$ as in the case of the $D_{BASE}$ data map, are previously stored as an A/F data map separately from the $D_{BASE}$ data map. After the searching of the target air-fuel ratio, whether or not the third gear of the five speed transmission is engaged is detected at a step 363. If the third gear is engaged, the searched value of the target air-fuel ratio is maintained. If the third gear is not engaged, whether or not the fourth gear is engaged is detected at a step 364. If the fourth gear is engaged, a value 0.4 is added to the searched target air-fuel ratio and a result of calculation is set as a new target air-fuel ratio at a step 365. If the fourth gear is not engaged, whether or not the fifth gear is engaged is in turn detected at a step 366. If the fifth gear is engaged, a value 0.6 is added to the searched value of the target air-fuel ratio and a result of the calculation is set as a new value of the target air-fuel ratio at a step 367. If the fifth gear is not engaged, it means that the shift position is any one of the first, second and the neutral position, and the CPU 37 determines that the A/F routine has completed and returns to the execution of the main routine. When the target air-fuel ratio $\lambda_T$ is set in this way, the target air-fuel ratio $\lambda_T$ is in turn supplied to the output latch 40 at a step 368. Since the output latch holds the target air-fuel ratio $\lambda_T$ in digital form and outputs provides it to the constant current supply circuit 41, a constant current having an intensity determined by the target air-fuel ratio is supplied to the oxygen pump element of the $O_2$ sensor 1 from the constant current supply circuit 41. In the above operations, if the shift position is any one of the first, second and the neutral position, the operation of the step 366 can be omitted since in that case the system detects, at the step 531, that the condition for the F/B control is not satisfied. In the above steps, the shift position is detected by means of the vehicle speed $V_H$ and the engine speed $N_e$ because regions of a ratio between the vehicle speed $V_H$ and the engine speed $N_e$ different from each other are obtained for the first to fifth gear of the transmission.

After the execution of the step 368, whether or not the electric potential generated by the cell element of the $O_2$ sensor 1 is smaller than the reference potential $V_r$ is detected at a step 537.

In other words, whether the air-fuel ratio of the mixture supplied to the engine 10, which is detected from the information of the oxygen concentration in the exhaust gas, is leaner than the target air-fuel ratio $\lambda_T$ is detected at a step 537. This detection is performed in such a manner that an oxygen concentration level $LO_2$ (output signal level of the $O_2$ sensor) is compared with a level $L\lambda$ corresponding to the target air-fuel ratio $\lambda_T$. If it is detected at the step 537 that the air-fuel ratio of the mixture is leaner than the target air-fuel ratio, a subtraction value $I_L$ is calculated at a step 538. The subtraction value $I_L$ is obtained by multiplication among a constant $K_1$, the engine speed $N_e$, and the absolute pressure $P_{BA}$, $(K_1 \cdot N_e \cdot P_{BA})$, and is dependent on the amount of the intake air of the engine 10. After the calculation of the subtraction value $I_L$, a correction value $I_{OUT}$ which is previously calculated by the execution of operations of the A/F routine is read out from a memory location $a_1$ in the RAM 39. Subsequently, the subtraction value $I_L$ is subtracted from the correction value $I_{OUT}$, and a result is in turn written in the memory location $a_1$ of the RAM 39 as a new correction value $I_{OUT}$, at a step 539.

On the other hand, if it is detected that the air-fuel ratio is richer than the target air-fuel ratio at the step 537 ($VO_2 \geqq V_r$), a summing value $I_R$ is calculated at a step 5310. The summing value $I_R$ is calculated by a multiplication among a constant value $K_2 (\neq K_1)$, the engine speed $N_e$, and the absolute pressure $P_{BA}$ ($K_2 \cdot N_e \cdot P_{BA}$), and is dependent on the amount of the intake air of the engine 10. After the calculation of the summing value $I_R$, the correction value $I_{OUT}$ which is previously calculated by the execution of the A/F routine is read out from the memory location $a_1$ of the RAM 39, and the summing value $I_R$ is added to the read out correction value $I_{OUT}$. A result of the summation is in turn stored in the memory location $a_1$ of the RAM 39 as a new correction value $I_{OUT}$ at a step 5311. After the calculation of the correction value $I_{OUT}$ at the step 539 or the step 5311 in this way, the correction value $I_{OUT}$ and the period of base duty ratio $D_{BASE}$ set at the step 533 are added together, and the result of the addition is used as the valve open period $T_{OUT}$ at a step 5312.

Additionally, after the reset of the time counter A and the start of the counting from the initial value at the step 535, if it is detected that the predetermined time period $\Delta t_1$ has not yet passed at the step 534, the operation of the step 5312 is immediately executed. In this case, the correction value $I_{OUT}$ calculated by the A/F routine up to the previous cycle is read out.

After the completion of the A/F routine, a valve close period $T_{AF}$ is calculated by subtracting the valve open period $T_{OUT}$ from the period of one duty cycle $T_{SOL}$ at a step 54. Subsequently, a value corresponding to the valve close period $T_{AF}$ is set in a time counter B incorporated in the CPU 37 (not shown), and down counting of the time counter B is started at a step 55. Then whether or not the count value of the time counter B has reached a value "0" is detected at a step 56. If the count value of the time counter B has reached the value "0", a valve open drive command signal is supplied to the drive circuit 36 at a step 57. In accordance with this valve open drive command signal, the drive circuit 36 operates to open the open/close solenoid valve 14. The opening of the open/close solenoid valve 14 is continued until a time at which the operation of the step 51 is performed again. If, at the step 56, the count value of the time counter B has not reached the value "0", the step 56 is effected repeatedly.

Figure 10:
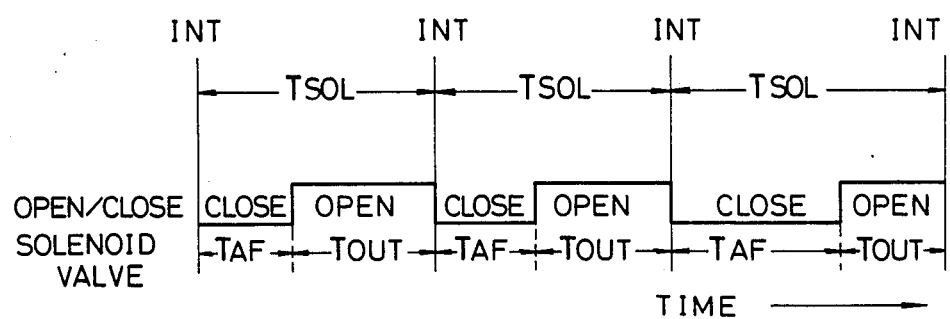
FIG. 10 is a timing chart showing the manner of operation of the system according to the invention generally shown in FIG. 4.

Thus, in the air intake side secondary air supply system according to the present invention, the open/close solenoid valve 14 is closed immediately in response to the generation of the internal interruption signal INT as illustrated in FIG. 10, to stop the supply of the air intake side secondary air to the engine 10. When the valve close time $T_{AF}$ for the open/close solenoid valve 14 within the period of one duty cycle is calculated and the valve close time $T_{AF}$ has passed after the generation of the interruption signal, the open/close solenoid valve 14 is opened to supply the air intake side secondary air to the engine through the air intake side secondary air supply passage 13. Thus, the duty ratio control of the supply of the air intake side secondary air is performed by repeatedly executing these operations. Further, the air-fuel ratio of the mixture to be supplied to the engine 10 is controlled to the target air fuel ratio by a duty ratio control of the supply of the air intake side secondary air.

Above, an embodiment of the oxygen concentration detection device according to the present invention and its application in an air-fuel ratio control system of an automotive internal combustion engine have been described.

Thus, according to the present invention, an oxygen concentration sensing device is constructed such that a constant current is supplied across the terminals of the oxygen pump element of an oxygen concentration sensor. An electric potential which develops across the terminals of the cell element is compared with a reference voltage at a comparator and an output signal of the comparator is used as an output signal of the device.

In this way, an oxygen concentration detection signal whose level is substantially proportional to the oxygen concentration of the exhaust gas is obtained by a very much simplified device. Further, in the application of the present invention which is explained with reference to FIGS. 4 through 10, the magnitude of the constant current supplied to the pump element is determined according to the target air-fuel ratio. However, it is to be noted that the output signal of the comparator is able to represent a result of comparison between the air-fuel ratio of the mixture supplied to the engine and the target air-fuel ratio by maintaining the level of the reference potential always constant without regard to the change in the target air-fuel ratio.

In the above explained application of the oxygen concentration sensing device according to the present invention, the air-fuel ratio control system was in the form of an air intake side secondary air supply system. However, it is be noted that the application of the present invention is not limited to this. For instance, the present invention is applicable to an air-fuel ratio control system in which the amount of fuel to be supplied to the engine is controlled.

What is claimed is:

1. An oxygen concentration sensing device for use in an air/fuel ratio control system for an internal combustion engine in which a target air/fuel ratio is determined in accordance with at least one of the operational parameters of said internal combustion engine and in which an air/fuel ratio of a supplied mixture is controlled toward the target air/fuel ratio in response to an oxygen concentration in the exhaust gas, comprising:

an oxygen concentration sensor unit disposed in an exhaust passage of said internal combustion engine, said oxygen concentration sensor unit including an oxygen pump element and a sensor cell element which define a restricted region therebetween and each of which comprises a solid electrolyte member having oxygen ion permeability and has a pair of electrodes provided on both sides thereof;

current supply means for supplying a pump current, which has a magnitude defined in accordance with the target air/fuel ratio, across the electrodes of said oxygen pump element thereby causing said sensor unit to generate a sensor voltage across the electrodes of said sensor cell element which is substantially in proportion to the oxygen concentration in the exhaust gas; and comparing means for comparing said sensor voltage with a predetermined reference voltage, and producing an output signal representing the result of the comparison as an oxygen concentration detection signal.

2. An oxygen concentration sensing device as set forth in claim 1 wherein said operational parameters are the engine rotational speed and the intake manifold vacuum.

* * * * *